(12) United States Patent
Mann et al.

(10) Patent No.: US 8,087,339 B2
(45) Date of Patent: Jan. 3, 2012

(54) ARMOR SYSTEM

(75) Inventors: Thomas Mann, Littleton, MA (US);
Denise Mahnken, Lunenburg, MA (US);
Michael E. McCormack, II, Hanson, MA (US); Martin Edward Smirlock, Concord, MA (US); Ronald E. Lundin, Handover, MA (US); Michael Coltrane, Andover, KS (US); Rick Scheer, Goddard, KS (US); Robert C. Sykes, Burlington, MA (US)

(73) Assignee: Foster-Miller, Inc., Waltham, MA (US)

( * ) Notice: Subject to any disclaimer, the term of this patent is extended or adjusted under 35 U.S.C. 154(b) by 227 days.

(21) Appl. No.: 11/999,345

(22) Filed: Dec. 5, 2007

(65) Prior Publication Data
US 2010/0083819 A1    Apr. 8, 2010

Related U.S. Application Data

(60) Provisional application No. 60/961,810, filed on Jul. 24, 2007.

(51) Int. Cl.
*F41H 5/04* (2006.01)
(52) U.S. Cl. .......................... 89/36.02; 89/904
(58) Field of Classification Search ............. 89/36.01, 89/36.02, 36.04, 36.05, 36.03; 428/911; 2/2.5
See application file for complete search history.

(56) References Cited

U.S. PATENT DOCUMENTS

| | | | | |
|---|---|---|---|---|
| 3,867,239 A * | 2/1975 | Alesi et al. | ...................... | 428/48 |
| 4,198,707 A * | 4/1980 | Haupt et al. | ...................... | 2/2.5 |
| 4,241,457 A * | 12/1980 | Klein et al. | ...................... | 2/2.5 |
| 4,633,756 A | 1/1987 | Rudoi | | |
| 4,664,967 A | 5/1987 | Tasdemiroglu | | |
| 4,928,575 A | 5/1990 | Smirlock et al. | | |
| 5,149,910 A | 9/1992 | McKee | | |
| 5,170,690 A | 12/1992 | Smirlock et al. | | |
| 5,191,166 A * | 3/1993 | Smirlock et al. | ............. | 89/36.02 |
| 5,217,185 A * | 6/1993 | Rucker | ........................ | 244/121 |
| 5,333,532 A | 8/1994 | Smirlock et al. | | |
| 5,456,156 A | 10/1995 | Semple | | |

(Continued)

FOREIGN PATENT DOCUMENTS

DE           3226476        7/1988

(Continued)

OTHER PUBLICATIONS

Written Opinion of the International Searching Authority for PCT Application No. PCT/US08/08918 mailed Mar. 30, 2009 (five (5) pages).

*Primary Examiner* — Bret Hayes
*Assistant Examiner* — Reginald Tillman, Jr.
(74) *Attorney, Agent, or Firm* — Iandiorio Teska & Coleman

(57) ABSTRACT

An armor system and method for the interior of a structure to be protected wherein releasable fastener material is secured to an inside wall of the structure and at least a first armor panel includes, in one example, a spacer layer, a ceramic hard face layer behind the spacer layer, a ballistic material behind the ceramic energy absorber layer, an encapsulant about the spacer layer, the ceramic energy absorber layer, and the ballistic material. Releasable fastener material is on the encapsulant adjacent the spacer layer for mating the panel to the inside wall of the structure.

9 Claims, 5 Drawing Sheets

U.S. PATENT DOCUMENTS

| | | | |
|---|---|---|---|
| 5,469,773 A | 11/1995 | Tarpinian | |
| H1519 H | 3/1996 | Semple | |
| 5,517,894 A | 5/1996 | Bohne et al. | |
| 5,556,695 A | 9/1996 | Mazelsky | |
| 5,560,971 A | 10/1996 | Emery | |
| 5,600,084 A | 2/1997 | Gonzalez | |
| 5,663,520 A | 9/1997 | Ladika et al. | |
| 5,679,918 A | 10/1997 | Korpi et al. | |
| 5,686,689 A | 11/1997 | Snedeker et al. | |
| 5,705,764 A * | 1/1998 | Schade et al. | 89/36.02 |
| 5,705,765 A | 1/1998 | Singh et al. | |
| 5,763,813 A | 6/1998 | Cohen et al. | |
| 5,771,489 A | 6/1998 | Snedeker | |
| 5,778,506 A | 7/1998 | Gonzalez | |
| 5,847,308 A | 12/1998 | Singh et al. | |
| 5,847,919 A | 12/1998 | Shimizu et al. | |
| 5,905,225 A | 5/1999 | Joynt | |
| 5,972,819 A | 10/1999 | Cohen | |
| 5,996,115 A | 12/1999 | Mazelsky | |
| 6,009,789 A | 1/2000 | Lyons | |
| 6,035,438 A | 3/2000 | Neal et al. | |
| 6,112,635 A | 9/2000 | Cohen | |
| 6,177,174 B1 | 1/2001 | Legrand | |
| 6,203,908 B1 | 3/2001 | Cohen | |
| 6,253,655 B1 | 7/2001 | Lyons et al. | |
| 6,289,781 B1 | 9/2001 | Cohen | |
| 6,298,765 B1 * | 10/2001 | Dvorak | 89/36.02 |
| 6,327,954 B1 | 12/2001 | Medlin | |
| 6,332,390 B1 | 12/2001 | Lyons | |
| 6,357,332 B1 | 3/2002 | Vecchio | |
| 6,389,594 B1 * | 5/2002 | Yavin | 2/2.5 |
| 6,405,733 B1 | 6/2002 | Fogarty et al. | |
| 6,408,734 B1 | 6/2002 | Cohen | |
| 6,497,966 B2 | 12/2002 | Cohen | |
| 6,523,450 B1 | 2/2003 | Schreiber | |
| 6,532,857 B1 | 3/2003 | Shih et al. | |
| 6,544,913 B2 | 4/2003 | Kim et al. | |
| 6,555,177 B1 | 4/2003 | Magnusson et al. | |
| 6,568,310 B2 | 5/2003 | Morgan | |
| 6,575,075 B2 | 6/2003 | Cohen | |
| 6,609,452 B1 | 8/2003 | McCormick et al. | |
| 6,679,157 B2 | 1/2004 | Chu et al. | |
| 6,698,331 B1 | 3/2004 | Yu et al. | |
| 6,718,861 B1 | 4/2004 | Anderson et al. | |
| 6,745,661 B1 | 6/2004 | Neal et al. | |
| 6,805,034 B1 | 10/2004 | McCormick et al. | |
| 6,860,186 B2 | 3/2005 | Cohen | |
| 6,899,009 B2 * | 5/2005 | Christiansen et al. | 89/36.02 |
| 6,920,817 B2 | 7/2005 | Ravid et al. | |
| 7,067,031 B2 | 6/2006 | deWitt | |
| 7,069,836 B1 | 7/2006 | Palicka et al. | |
| 7,070,242 B2 | 7/2006 | Mears et al. | |
| 7,077,048 B1 | 7/2006 | Anderson et al. | |
| 7,077,306 B2 | 7/2006 | Palicka et al. | |
| 7,104,177 B1 | 9/2006 | Aghajanian et al. | |
| 7,117,780 B2 | 10/2006 | Cohen | |
| 7,128,963 B2 | 10/2006 | Benitsch | |
| 7,157,158 B2 | 1/2007 | Collier et al. | |
| 7,180,302 B2 | 2/2007 | Kelsey et al. | |
| 7,188,559 B1 | 3/2007 | Vecchio | |
| 7,210,390 B1 * | 5/2007 | Olson et al. | 89/36.05 |
| 7,225,717 B2 | 6/2007 | Williams | |
| 7,793,579 B1 * | 9/2010 | Lee | 89/36.02 |
| 2003/0192426 A1 | 10/2003 | Peretz | |
| 2003/0221547 A1 | 12/2003 | Peretz | |
| 2005/0262999 A1 | 12/2005 | Tomczyk et al. | |
| 2007/0017359 A1 | 1/2007 | Gamache et al. | |
| 2007/0111621 A1 | 5/2007 | Barsoum et al. | |
| 2007/0113729 A1 | 5/2007 | Monk et al. | |
| 2007/0137471 A1 * | 6/2007 | Mazur | 89/36.02 |
| 2008/0264243 A1 * | 10/2008 | Lucuta et al. | 89/36.02 |
| 2008/0271595 A1 * | 11/2008 | Bird et al. | 89/36.02 |

FOREIGN PATENT DOCUMENTS

| | | |
|---|---|---|
| DE | 102004060267 | 6/2006 |
| EP | 0334263 | 9/1989 |
| EP | 0578085 | 1/1994 |
| GB | 2390578 | 1/2004 |

* cited by examiner

ARMOR SYSTEM

RELATED APPLICATIONS AND PRIORITY CLAIM

The subject application claims the benefit of and priority to U.S. Provisional Application No. 60/961,810, filed Jul. 24, 2007.

FIELD OF THE INVENTION

This subject invention relates to armor.

BACKGROUND OF THE INVENTION

Armor configured to be added to a structure such as a vehicle is well known. The applicant hereof invented the idea of ceramic armor tiles removably attached to the outside of a vehicle. See U.S. Pat. Nos. 4,928,575 and 5,191,166 incorporated herein by this reference.

Typically, for armor inside of the vehicle, a flexible spall barrier or liner is used. See U.S. Pat. Nos. 5,170,690 and 5,333,532 incorporated herein by this reference.

Sometimes, for certain structures facing specific threats, armor on the outside of the structure is not possible or desirable and/or a flexible spall barrier or liner on the inside of the structure does not provide sufficient protection.

U.S. Pat. No. 4,664,967 discloses a more rigid spall liner with layers of fabric and steel. Published Patent Application No. 2003/0192426 discloses armor panels including ceramic designed to be placed on the inside of a vehicle door. See also published Patent Application No. 2007/0113729 and DE 3226476. All of these references are incorporated herein by this reference.

Despite the state of the art in armor design, a need still exists for a suitable armor system which can be placed on the inside of a structure for protecting the same from different threats.

BRIEF SUMMARY OF THE INVENTION

It is therefore an object of this invention to provide a new armor system for the interior of a structure.

It is a further object of this invention to provide such an armor system which is easily installed and removed without modification of the parent (existing) structure.

It is a further object of this invention to provide such an armor system which adequately protects against a number of different threats.

It is a further object of this invention to provide such an armor system which is easier to handle and transport.

It is a further object of this invention to provide such an armor system which is easier and less expensive to manufacture.

The subject invention results from the realization, in part, that, in one example, a better armor system for the interior of a structure such as a ground vehicle, aircraft, or watercraft includes suitable armor materials spaced from the interior of the structure by a spacer layer and all encapsulated in a polyurea/polyurethane coating resulting in panels which are easier to handle, transport, and install since hook and loop fasteners are used on the inside of the structure and on the panels. In one embodiment, the armor materials include a ceramic layer and one or more ballistic layers. In another example, the armor materials include ballistic layers but no ceramic.

The subject invention features an armor system for the interior of a structure to be protected. The typical system includes releasable fastener material secured to an inside wall of the structure and at least a first armor panel. One preferred panel includes an optional spacer layer, a ceramic hard face layer behind the spacer layer, ballistic material behind the ceramic hard face layer, an encapsulant about the spacer layer, the ceramic hard face layer, and the ballistic material, and releasable fastener material on the encapsulant adjacent the spacer layer for mating the panel to the inside wall of the structure.

In one example, the spacer layer includes foam and the ceramic hard face layer includes an aluminum oxide ceramic material. The ballistic material may include a composite laminate such as plies of aramid fibers. In one example, the ballistic material includes a thermoplastic matrix material or high performance and high molecular weight polyethylene. The typical encapsulant includes a polyurea/polyurethane. The typical releasable fastener material includes hook and loop fasteners.

The armor system may also include a second armor panel and a joint between the first armor panel and the second armor panel. In one example, the first panel includes a lap portion and the second panel includes a tongue portion receivable over the lap portion of the first panel. The lap portion of the first panel typically includes an edge without the spacer layer. The tongue portion of the second panel typically includes a ceramic layer and a ballistic layer. In another example, the first panel and the second panel include lap portions and the system further including a tongue member bridging the lap portions of the first and second panels. The lap portion of each panel includes an edge without a spacer layer and preferred tongue member includes a ceramic layer and a ballistic layer.

An armor panel in accordance with the subject invention includes an optional spacer layer, a ceramic hard face layer behind the spacer layer, ballistic material behind the ceramic hard face layer, an encapsulant about the spacer layer, the ceramic hard face layer, and the ballistic material, and releasable fastener material on the encapsulant adjacent the spacer layer for mating the panel to an inside wall of a structure.

Another armor panel in accordance with the subject invention includes an optional spacer layer, ballistic material behind the spacer layer, an encapsulant about the spacer layer and the ballistic material, and releasable fastener material on the encapsulant adjacent the spacer layer for mating the panel to an inside wall of a structure.

The subject invention also features a method of making an armor panel. In one example, a ceramic hard face layer is assembled on ballistic material, an optional spacer layer is assembled on the ceramic layer, and an encapsulant is sprayed about the layers to form a panel.

One method of protecting a structure features securing releasable fastener material to an inside wall of the structure, supplying an armor panel including an optional spacer layer, a hard face absorber layer behind the spacer layer, ballistic material behind the hard face absorber layer, an encapsulant about all the layers, and a releasable fastener material on an encapsulant adjacent the spacer layer, and mating the releasable fastener material on the panel to the releasable fastener material on the structure to secure the panel to the inside wall of the structure.

Another method of making an armor panel includes assembling an optional spacer layer on ballistic material and spraying an encapsulant about the spacer layer and the ballistic material to form a panel.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
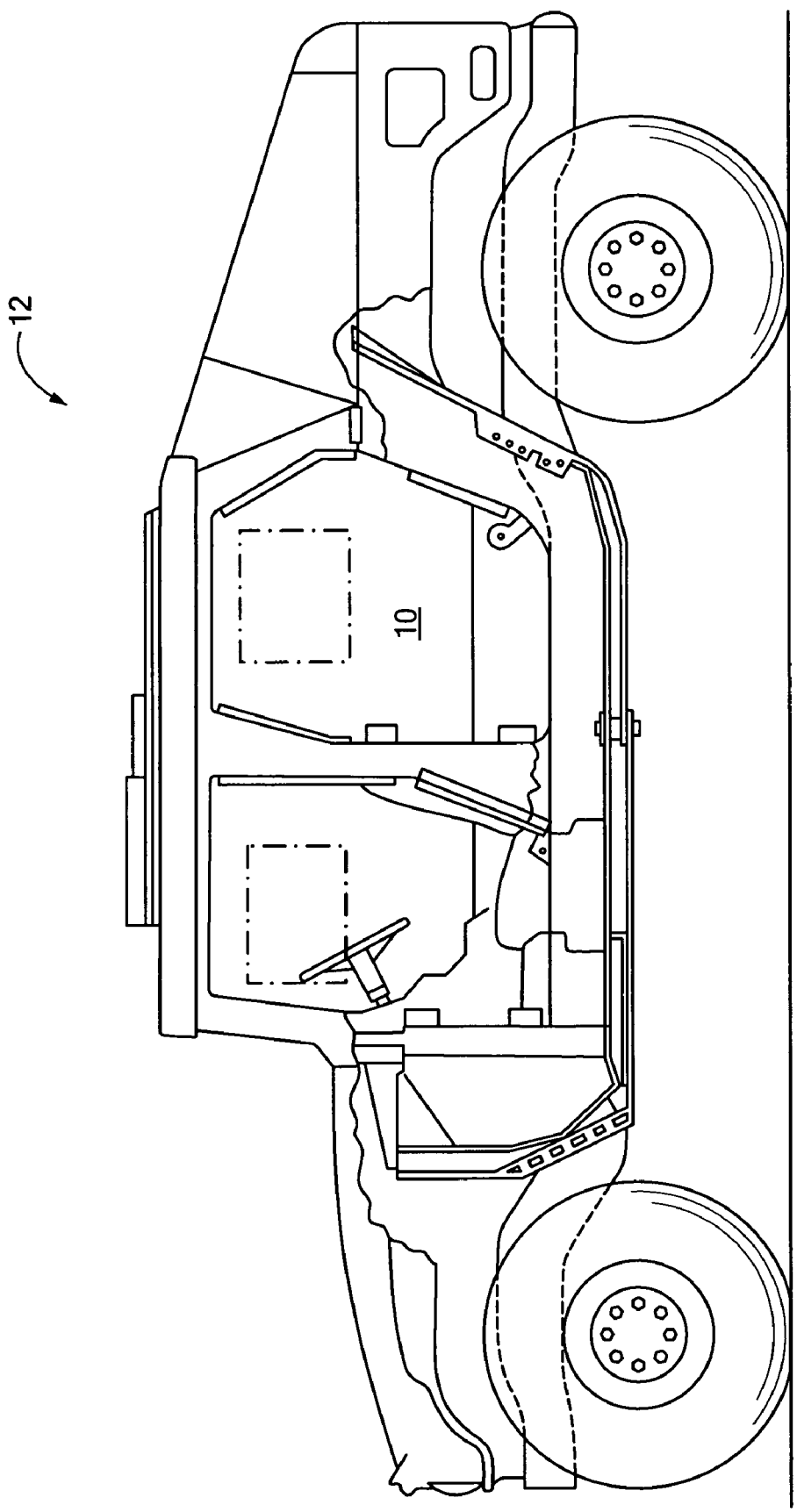
FIG. 1 is a schematic side view of a typical army vehicle with one or more door panels which may be protected via the armor panels of the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows one of many structures that may be protected by the armor system of the subject invention. The interior of the door panels of this military vehicle may be protected by the armor system hereof and so too may the floor, sides, rear and ceiling, if desired. Other structures to be protected by the subject invention include aircraft, vessels, and even fixed structures such as command centers, bunkers, barracks, and check stations. Typically, the armor panels are manufactured to match the overall shape of the interior of a structure. For example, one armor panel may be configured in the same shape as the interior of door 10 of vehicle 12 while another may be manufactured in general shape of a seat cushion or a floor area, or the like.

Figure 2:
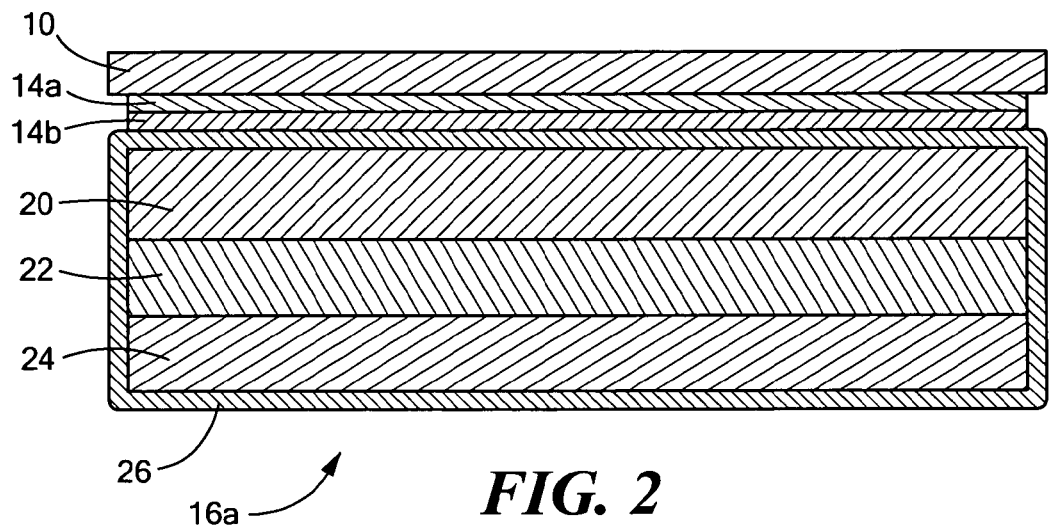
FIG. 2 is a highly schematic cross-sectional side view showing an armor panel in accordance with the subject invention releasably attached to the interior of the door of the military vehicle shown in FIG. 1.
Figure 3:
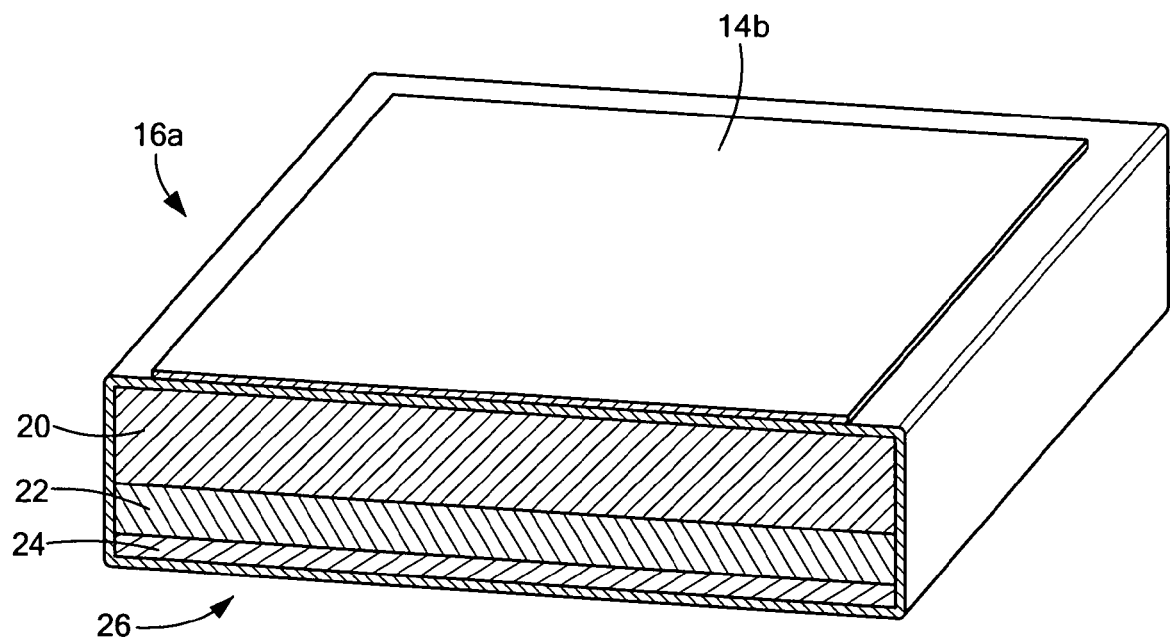
FIG. 3 is a highly schematic three-dimensional cut-away view showing the primary components associated with a typical armor panel in accordance with the subject invention.

In FIG. 2, wall 10 represents the door of the vehicle or some other portion of a structure. Releasable fastener material such as hook and loop fastener structure (e.g., the well-known material manufactured under the Velcro® brand name) of a first type (e.g., hooks) 14a is secured (using an adhesive, a tape, or a glue) on the interior of door 10. Hook and loop fastener material of a second type (e.g., loops) 14b is on armor panel 16a (again, using a tape, glue, or adhesive). In this particular example, as also shown in FIG. 3, panel 16a includes optional spacer layer 20 (e.g., open faced Elliot P300 foam), ceramic hard face layer 22 (e.g., a layer of aluminum oxide ceramic material), and ballistic material 24. Ballistic material 24 may include plies of aramid or aromatic polyamide fibers, such as KEVLAR® aramid consolidated within a thermoset or thermoplastic matrix material. The ballistic material may also be high performance and high modulus polyethylene such as DYNEEMA® or Spectra Shield®, or other high strength ballistic fiber material in consolidated or unconsolidated (soft) form.

Irrespective of the internal construction of the armor panel, it is preferred that the individual components are secured together in a panel form by encapsulant 26 which is typically sprayed about the top, bottom, and sides of the lay-up completely covering it. In one embodiment, a grey polyurea/polyurethane material sold under the commercial name "Line-X" was used. This material is typically used to coat and protect the bed of a pick up truck. Other hardenable polymers may also be used.

In one 2'×2' test panel, foam layer 20 was 1 inch thick, ceramic layer 22 was 16 mm thick, and ballistic material 24 was ½ inch thick. The grey encapsulant material was sprayed on to a thickness of 0.06 inches.

Figure 4:
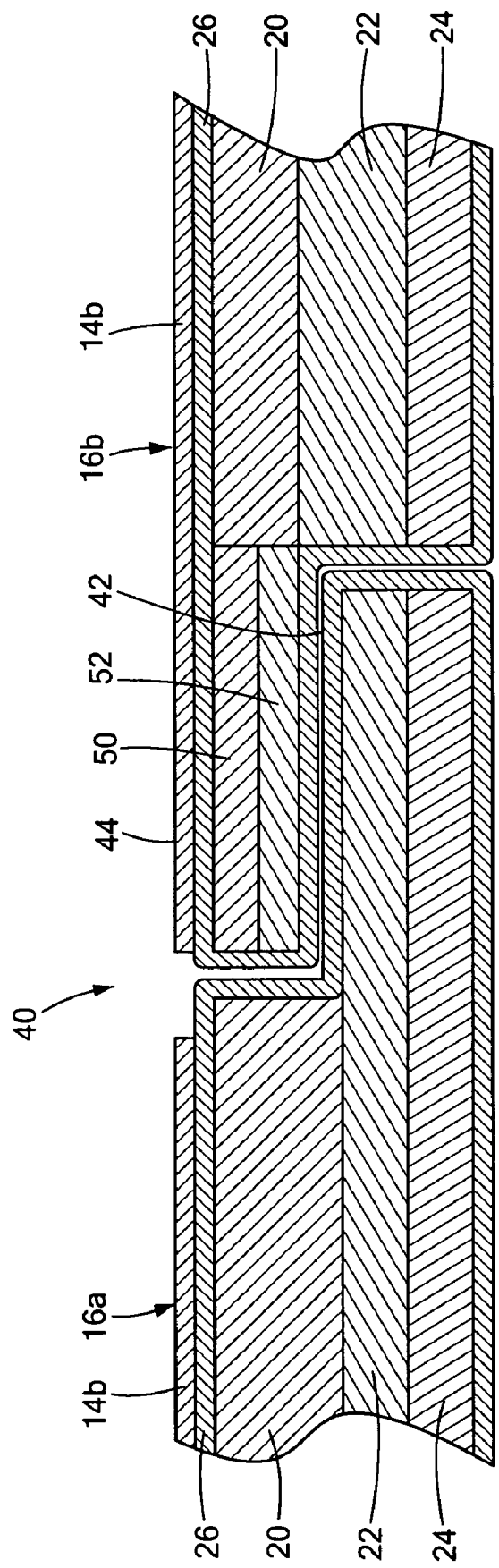
FIG. 4 is a schematic cross-sectional view showing two armor panels in accordance with the subject invention and a half lap joint therebetween.

Sometimes, more than one panel is used to protect an interior wall or portion of a structure. FIG. 4 shows two panels 16a and 16b and one example of a joint 40 therebetween. First panel 16a includes lap portion 42 and second panel 16b includes tongue portion 44 received on lap portion 42. In one particular example, lap portion 42 includes an edge of panel 16a without foam layer 20. Tongue portion 44 of panel 16b includes ceramic layer 50 and ballistic material 52. Again, all the layers are encapsulated in material 26. Ceramic layer 50 may be 0.5 inches thick and ballistic material 52 may be 0.5 inches thick.

Figure 5:
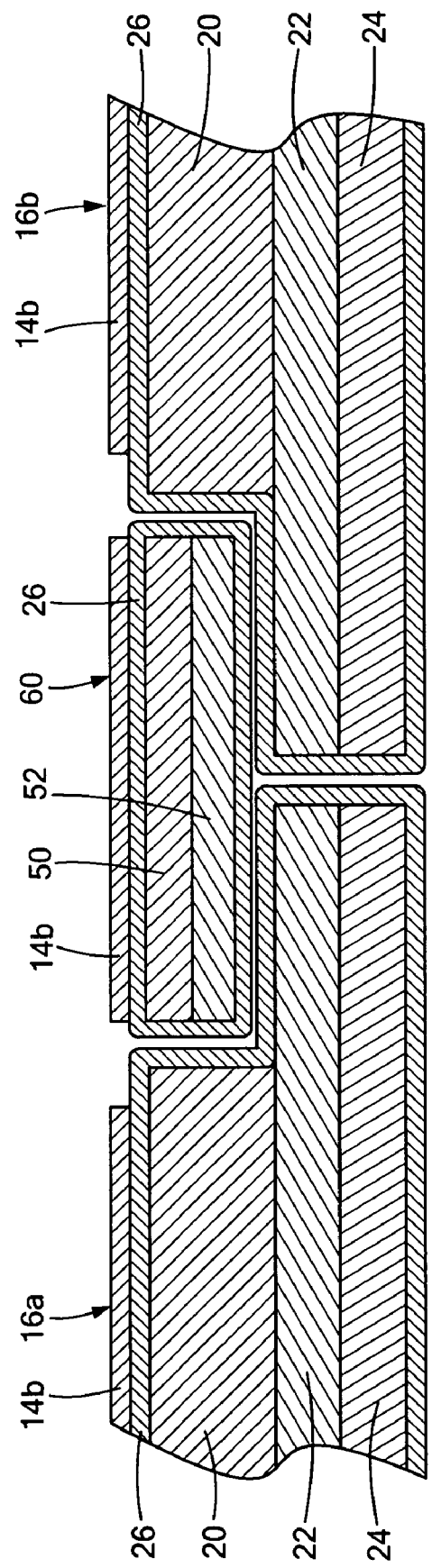
FIG. 5 is a schematic cross-sectional view also showing two adjacent panels in accordance with the subject invention and a different kind of protected joint between the panels.

FIG. 5 shows two adjacent panels 16a and 16b in another example where both of the panels include an edge lap portion where an edge of each panel is devoid of foam layer 20. Separate tongue member 60 is located so it bridges the lap portions of panels 16a and 16b as shown. Tongue member 60 may include ceramic layer 50 and ballistic material 52 encapsulated within polyurea/polyurethane layer 26. Tongue member 60 can be secured to the panels 16a and/or 16b using an adhesive or hook and loop fasteners if desired. Also, separable fastener structure such as hook and loop fastener material 14b can be added to tongue member 60 as shown.

Figure 6:
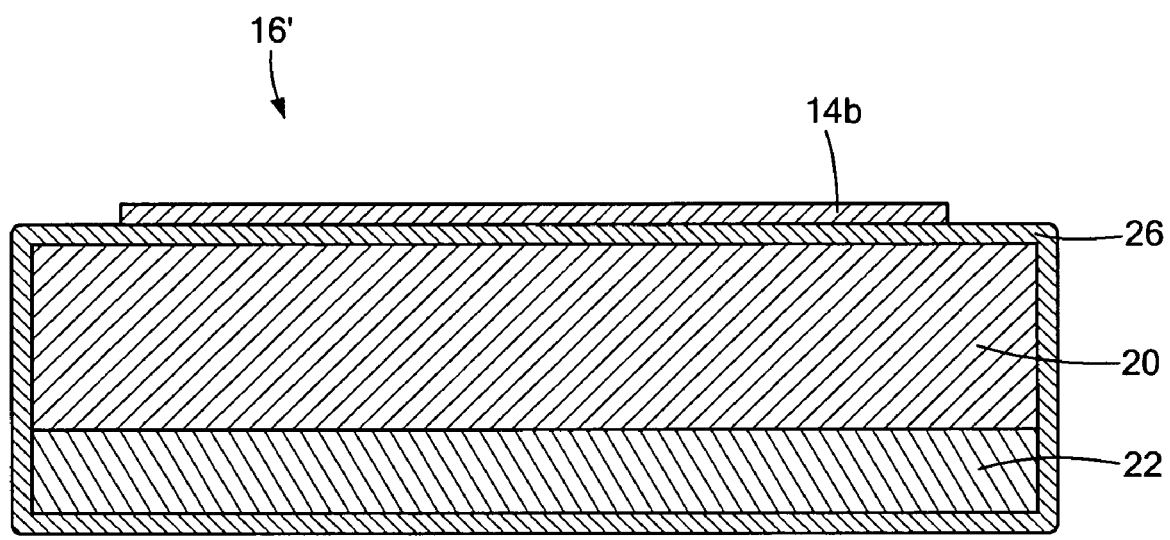
FIG. 6 is a schematic cross-sectional view showing the primary components associated with an example of another embodiment of an armor panel in accordance with the subject invention.

In another example, panel 16', FIG. 6 includes optional spacer layer 20 (e.g., foam) and ballistic material 24 encapsulated within polyurea/polyurethane coating 26. Again, hook and loop fastener material 14b is typically used to secure panel 16' to the interior of a structure. In one specific test panel, foam layer 20 was 1.0 inches thick and ballistic material 24 included a high modulus polyethylene (DYNEEMA®) 1.0 inches thick.

The result, in any embodiment, is an armor system for the interior of a structure which is easily installed and removed and yet still provides adequate protection against a number of different types of threats. Due to the panel configuration of the armor system, a number of panels which could completely line in the interior of a structure are easier to handle and transport. The use of the encapsulation spray-on coating provides structural integrity to the panel while also making the panels less expensive and easier to manufacture.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An armor system comprising:
    a first armor panel including:
        a main portion comprising, in cross-section,
            a releasable fastener on an encapsulant,
            a spacer layer behind the encapsulant,
            hard face material behind the spacer layer,
            ballistic material, and
            the encapsulant on the ballistic material,
        a lap portion without the spacer layer of the main portion and including, in cross-section,
            the encapsulant,
            hard face material behind the encapsulant,
            ballistic material behind the hard face material, and
            the encapsulant on the ballistic material; and
    a second adjoining armor panel comprising:
        a main portion including, in cross-section,
            a releasable fastener on an encapsulant,
            a spacer layer behind the encapsulant,
            hard face material behind the spacer layer,
            ballistic material, and
            the encapsulant on the ballistic material, and
        a tongue portion over the lap portion of the first armor panel, the tongue portion different in composition than the main portion of the second armor panel and including, in cross-section,
            the encapsulant,
            ballistic material, and
            the encapsulant on the ballistic material,
            the encapsulation about an exterior of first armor panel and the second armor panel.

2. The armor system of claim 1 in which the tongue portion of the second armor panel further includes hard face material on the ballistic material.

3. The armor system of claim 1 in which the hard face material includes ceramic material.

4. The armor system of claim 1 in which the spacer layer includes foam.

5. The armor system of claim 1 in which the encapsulant includes a hardened polymer material.

6. An armor system comprising:
    a first armor panel including:
        a main portion comprising, in cross-section,
            a releasable fastener on an encapsulant,
            hard face material,
            ballistic material, and
            an encapsulant on the ballistic material,
        a lap portion including, in cross-section,
            an encapsulant,
            hard face material behind the encapsulant,
            ballistic material behind the hard face material, and
            the encapsulant on the ballistic material; and
    a second adjoining armor panel comprising:
        a main portion including, in cross-section,
            a releasable fastener on the encapsulant,
            hard face material,
            ballistic material, and
            the encapsulant on the ballistic material, and
        a tongue portion over the lap portion of the first armor panel, the tongue portion different in composition than the composition of the main portion of the second armor panel and including, in cross-section,
            the encapsulant,
            ballistic material, and
            the encapsulant on the ballistic material, the encapsulant about an exterior of the first armor panel and the second armor panel.

7. The armor system of claim 6 in which the first armor panel main portion and second armor panel main portion both include a spacer layer behind the encapsulant and the hard face material.

8. The armor system of claim 6 in which the tongue portion of the second armor panel further includes hard face material on the ballistic material.

9. The armor system of claim 6 in which the encapsulant includes a hardened polymer material.

* * * * *